United States Patent
Stroh et al.

(10) Patent No.: US 6,821,762 B2
(45) Date of Patent: Nov. 23, 2004

(54) REACTOR MODULE WITH CAPILLARY MEMBRANES

(75) Inventors: Norbert Stroh, Magstadt (DE); Thomas Graeve, Stuttgart (DE)

(73) Assignee: Fraunhofer-Gesellschaft zur Forderung der Angewandten Forschung E.V. (DE)

( * ) Notice: Subject to any disclaimer, the term of this patent is extended or adjusted under 35 U.S.C. 154(b) by 0 days.

(21) Appl. No.: 10/276,098

(22) PCT Filed: Apr. 14, 2001

(86) PCT No.: PCT/EP01/04271

§ 371 (c)(1), (2), (4) Date: Jun. 20, 2003

(87) PCT Pub. No.: WO01/88083

PCT Pub. Date: Nov. 22, 2001

(65) Prior Publication Data

US 2004/0048366 A1 Mar. 11, 2004

(30) Foreign Application Priority Data

May 13, 2000 (DE) .......................................... 100 23 505

(51) Int. Cl.[7] .............................................. C12N 11/00
(52) U.S. Cl. .................... 435/174; 435/176; 435/289.1; 435/297.4
(58) Field of Search ................. 435/174, 176, 435/289.1, 297.4

(56) References Cited

U.S. PATENT DOCUMENTS

| 4,720,462 A | * | 1/1988 | Rosenson | 435/286.6 |
| 4,948,728 A | * | 8/1990 | Stephanopoulos et al. | 435/41 |
| 5,416,022 A | | 5/1995 | Amiot | |
| 5,512,474 A | | 4/1996 | Clapper et al. | |
| 5,981,272 A | | 11/1999 | Chung | |

FOREIGN PATENT DOCUMENTS

| CH | 631207 | * | 7/1882 |
| DE | 3409501 | * | 10/1985 |
| DE | 3637260 A1 | * | 5/1988 |
| DE | 4222345 | * | 1/1994 |
| DE | 4116727 | * | 9/1995 |
| DE | 19810901 | * | 6/1999 |
| EP | 0217848 | * | 6/1989 |
| EP | 0413027 | * | 7/1989 |
| GB | 2159729 | * | 12/1985 |
| JP | 64-20081 | | 1/1989 |
| JP | 6-14764 | | 1/1994 |
| WO | WO 84/01959 | * | 5/1984 |
| WO | WO 90/02170 | * | 3/1990 |
| WO | WO 01/09607 A1 | * | 8/2001 |

OTHER PUBLICATIONS

CAPLUS 114; 1991;:203112/DN.

* cited by examiner

*Primary Examiner*—David A. Redding
(74) *Attorney, Agent, or Firm*—Dickstein, Shapiro, Morin & Oshinsky, LLP.

(57) ABSTRACT

The present invention relates to a reactor module constructed of hollow fibers and cells as well as to reactors comprising this reactor module.

15 Claims, 2 Drawing Sheets

REACTOR MODULE WITH CAPILLARY MEMBRANES

This application is based on PCT/EP01/04271, filed Apr. 14, 2001, and claims priority to German Patent Application Number 10023505.0, filed May 13, 2000.

FIELD OF THE INVENTION

The present invention describes a reactor module able to function as a component of an artificial organ as well as a reactor containing this reactor module.

BACKGROUND OF THE INVENTION

Diseases, especially of internal organs, occur often in humans and are often life-threatening. Organ transplantations are often needed, and often fail due to the limited availability of natural replacement organs. External systems for supporting the damaged or failed organ functions often prove to be insufficient, since they significantly reduce the patient's quality of life, and are also unable to participate in the biochemical processes of the body. Looking at the example of the liver, during recent years, hybrid life support systems have been developed. With these systems, liver cells are cultivated in artificial modules, whereby different metabolism, elimination, and synthesis processes of the liver may be replaced in patients with acute liver failure. The existing systems are based on an extracorporal circuit to which the patient is connected. The reactor used consists of a housing in which the liver cells are located. The patient's blood or plasma is in direct contact with the cells. It is hereby known that the hepatocytes are immobilized in or on small spheres, for example alginate (Selden et al., Ann N Y Acad Sci (1999) 875, 353–363; Naka et al, Artificial Organs (1999) 23, 822–828, and Sakai et al., Cell Transplantation (1999) 8, 531–541). Also known is the simulation of the parenchymal structure of the liver with multi-dimensionally arranged capillary bundles (Custer and Mullon, Adv Exp Med Biol (1998) 454, 261–271; Busse and Gerlach, Ann N Y Acad Sci (1999) 875, 326–339, Flendrig et al., Int J Artif Organs (1999) 22, 701–708; Margulis et al., Resuscitation (1989) 18, 85–94; Ellis et al., Hepatology (1996) 24, 1446–1451; Gerlach et al., Transplantation (1994) 58, 984–988).

The described artificial organs, in which natural cells are immobilized on a sub-structure, for example polymer hollow fibers or capillaries, have the disadvantage that the cells often can only be immobilized with difficulties. The reason for this is, among other things, that the fluctuations in diameter that are associated with flow-through pulses in the polymer hollow fibers usually make immobilization more difficult and also could lead to denaturation effects in the cells.

SUMMARY OF INVENTION

The present invention is therefore based on the technical problem of making available a reactor module for use in artificial organs that overcomes said disadvantages.

The present invention solves the underlying technical problem by providing a reactor module, comprising at least one ceramic hollow fiber and at lest one biological cell, whereby at least one biological cell is immobilized on the surface of the at least one ceramic hollow fiber. In an especially preferred embodiment, the at least one biological cell is a liver cell, i.e. a hepatocyte. Naturally, other cells, for example renal cells, conjunctive tissue cells, fibroblasts, immune cells, intestinal cells, skin cells, pancreatic cells, spleen cells, or blood cells also can be used according to the invention.

In another preferred embodiment of the invention, many cells, in particular a cell layer, in particular a monolayer, are immobilized on the surface of the at least one ceramic hollow fiber.

The invention is among other reasons advantageous in that the inherent stiffness of the used ceramic hollow fibers enables its defined spatial positioning within a reactor space. In contrast to polymer hollow fibers or capillaries, this does not result in fluctuations in the diameter associated with flow-through pulses, so that the immobilized cells cannot be negatively affected. The ceramic hollow fibers can be adapted with respect to their geometry, their outer and inner diameter, and their porosity and pore size to any cell species, thus making the reactor module according to the invention suitable for many applications. In addition, the ceramic hollow fiber provides a surface that can be modified with many different processes of a physical and electrical or chemical nature. This makes it possible to achieve improved immobilization of the cells. Finally, ceramic hollow fibers have pores that enable a removal of metabolic products and, as the case may be, also the supply of nutrients.

According to the invention, it is provided that the cells to be immobilized are brought into contact with the ceramic hollow fibers, grow onto the surface of the hollow fibers, proliferate, and form a monolayer. The toxic metabolic products emitted by the immobilized cells are able to reach the inside of the hollow fibers via the defined pores contained in the hollow fibers, and can be removed from there, or can be supplied via the defined pores with nutrients from inside the hollow fibers.

In connection with the present invention, a biological cell means the structural and functional unit of the organisms, which is characterized by its growth, proliferation, and metabolic capability. Such cells can be eukaryotic cells, such as animal, plant, or yeast cells. In connection with the present invention, cells also mean prokaryotic cells, such as bacteria cells. In an especially advantageous embodiment, the cells are human or animal cells, in particular liver cells, fibroblasts, connective tissue cells, intestinal cells, blood cells, immune cells, skin cells, spleen cells, kidney cells, or pancreatic cells. Naturally, the cells may also be naturally occurring cells or cells manipulated with gene technology. The cells may be healthy or diseased, for example immortalized or carcinogenic. The cells may be differentiated or dedifferentiated, omnipotent, pluripotent, or unipotent.

In connection with the present invention, an immobilization means a spatial fixation of the at least one biological cell on or at the surface of the ceramic hollow fiber. The immobilization may be reversible or irreversible. It may be performed by simple cultivation and growing to the surface of the hollow fiber, but may also be brought about or accelerated with chemical or physical processes.

In connection with the present invention, a ceramic hollow fiber means a hollow fiber made from ceramic materials, i.e. a hollow fiber consisting of inorganic and primarily non-metallic compounds or elements that preferably contains more than 30% by volume of crystalline materials. According to the invention, both oxidic as well as non-oxidic ceramic materials can be used. Such non-oxidic materials, for example, may include silicium carbide SiC or silicium nitride $Si_3N_4$ that may be produced, for example, by pyrolysis from polycarbosilanes or, respectively, from polysilazanes. Naturally, it is also possible to produce oxidic ceramic membranes with hollow fiber geometry, whereby, for example, a ceramic powder is mixed with a binder, and this pasty mass is extruded. This is followed by sintering, whereby a dense green fiber with a ceramic structure is produced, whose pore size may be varied depending on various parameters, such as amount and nature of the sintered binder, the sinter regime, the powder morphology, etc.

It may also be provided that ceramic materials with cellulose as a binder are used, whereby these are dissolved in a solvent, for example N-methyl-morpholine-N-oxide (NMMNO). This cellulose solution is mixed with ceramic powder and further processed in an actually known manner (DE 4426966 TITK of Feb. 1, 1996).

In another embodiment, the invention furthermore relates to a previously mentioned reactor module, whereby the capillary membranes have an inner diameter of 0.1 to 4 mm, preferably 0.5 to 1 mm. In another embodiment, the pore size of the hollow fiber used in the reactor module according to the invention is 0.05 to 1 $\mu$m, preferably 0.1 to 0.5 $\mu$m.

In another embodiment of the present invention, the surface of the hollow fibers is modified. The modification provided according to the invention permits an improved immobilization of the cells in vitro. The surface modification may be performed using chemical and physical, in particular thermal or electrical processes. It may be provided, for example, to use chemical processes such as radical or ionic graft copolymerization, simple coatings, or gas phase processes, such as low-pressure or low-temperature plasma technology. The use of low-pressure plasma processes is hereby especially preferred, since it allows both defined changes of the physical surface properties, such as roughness, as well as of the chemical composition of the surface in a single step. The plasma treatment that is especially preferred according to the invention permits a free selection of the substrate material, a defined adjustment of surface properties without changing volume characteristics; uses only small amounts of chemicals as a result of the physical vacuum process, and makes it possible to perform the process in a dry, closed system. Plasma, also an ionized gas with the exact same number of positive and negative charges, can be used for ionization over a very wide range of pressures and temperatures. According to an especially preferred embodiment of the present invention, low-pressure plasma with a pressure from 0.01 to 1 mbar is used for surface modification. The plasma atmosphere consists of free electrons, radicals, ions, UV radiation, and a large number of particles excited in different manners. By choosing the concentration of the chemical composition of the monomers introduced into the gas chamber, the dwelling time of the molecules in the reaction space, the input high-frequency power, and the electrostatic charge of the treated material, the formation of the new surface can be determined in a defined manner (Strobel et al., Plasma surface modification of polymers: Relevance to adhesion, Utrecht (1994)). The treatment time provided according to the invention may be varied according to requirements; however, in an especially preferred embodiment it ranges from 1 second to 10 minutes, preferably 4 seconds to 5 minutes. By using the low-pressure plasma technology provided according to the invention, the surface can be cleaned and an etching abrasion can be achieved, the micro-roughness can be modified, the formation of radical points and subsequent secondary reactions, such as cross-linking processes or graft copolymerization, as well as plasma polymerization and thus the formation of homogeneous, adhesive films in the nanometer range can be achieved.

According to the invention, a preferred embodiment also provides the surface with functional groups, for example hydrophobic, anionic, cationic, for example amino groups, or polarized groups and/or with polypeptides or proteins. This includes in particular matrix proteins, such as fibronectin, laminin, or collagen.

According to the invention, the surface of the hollow fibers may be provided with adhesion promoters, such as integrins, fibronectin, vitronectin, and/or collagen in order to facilitate the immobilization of the cells.

In an especially preferred embodiment of the present invention, the surface may be provided with a primer layer with, for example, SiOx stoichiometry. This represents an interface layer—from organic to inorganic, from silicone to glass—to which other groups can be bonded very easily. This primer coat then can be functionalized with nitrogen-containing groups, for example with functional groups, in particular amino groups. It would also be conceivable according to the invention to provide other surfaces, in particular cationic surfaces. Naturally, the primer layer can be connected via spacers or linkers with the functional groups.

In another embodiment of the present invention, the ceramic hollow fibers are arranged parallel to each other in one plan in a frame, whereby the hollow fibers are connected with each other in series or are present separately from each other. The frame may consist of plastic, for example polystyrene, polymethyl methacrylate, polycarbonate, or polypropylene or may contain substantial parts of it. In a special embodiment of the present invention, the reactor module according to the invention is realized in the form of a preferably square or rectangular disk. The arrangement of the hollow fibers according to the invention in one plane, for example in mats, makes it possible to avoid the risk of "tunneling" associated with the flow through the external space and thus a reduction in efficiency.

In another embodiment, thermal compensation elements, for example of fiberglass or carbon fiber strands, may be provided in the frame of the reactor module, said compensation elements accounting both for thermal tensions occurring, for example, during sterilization or freezing, and for the different materials used.

In another preferred embodiment of the present invention, this also relates to a reactor comprising at least one previously mentioned reactor module, particularly in disk shape, and a housing. According to the invention, several of the preferably disk-shaped reactor modules must be arranged in layers at defined intervals in such a way relative to each other that a required surface can be composed by layering a sufficient number of such disk-shaped reactor modules. The inlet and outlet of the flowing media can be implemented with a connection system, as is used, for example, in standard electrodialysis modules. The end pieces contain the corresponding connections through which the individual channels, formed by recesses in the disk-shaped reactor modules, can be supplied.

In a preferred embodiment of the present invention, the frames of the modules have openings that may serve as inlet or outlet openings for the metabolic products or nutrients. According to the previously described embodiment, in which several reactor modules are arranged serially in a reactor, the frames of the modules at the same time form the outside wall of the reactor. The housing is provided in its terminal areas with inlet and outlet openings for the fluid, for example plasma, passing through the reactor. Depending on the orientation of the serially arranged frames in relation to each other, the inlet and outlet openings for the fluid in the terminal areas of the frame present channels in the outer reactor wall that is formed by the frames, through which channels a targeted addition or removal of substances into certain areas of the reactor is made possible. This means that by placing several reactor modules behind each other in a suitable manner, supply and removal channels for the reactor inside space, which comprises both the extracapillary and intracapillary space, can be formed, in this way enabling a functional and spatial compartmentalization. In this way, different, serially provided cultivation conditions may be provided for the same or different cells in order to enable an organ function that is as efficient and as versatile in its control as possible.

In an especially preferred embodiment of the present invention, the reactor furthermore has oxygenation, heat exchanger and/or sample collection units or inoculation access points. In an especially preferred embodiment of the present invention, the reactor inside space is closed off with sterile filters located in the area of the terminal areas in order to prevent a flushing out of cells and cell components into the patient circuit.

The reactor according to the invention may be used, for example, to construct an artificial liver, whereby the reactor is connected together with pumps and plasma separators into an extracorporal circuit involving also the patient. In such a preferred embodiment, the reactor according to the invention is preceded by a plasma separator or is integrated in such a plasma separator in order to enable a cell-free operation of the reactor.

Other advantageous embodiments of the invention derive from the secondary claims.

BRIEF DESCRIPTION OF THE DRAWINGS

The invention is explained in detail in reference to the following example and associated figures.

DETAILED DESCRIPTION OF THE INVENTION

Figure 1:
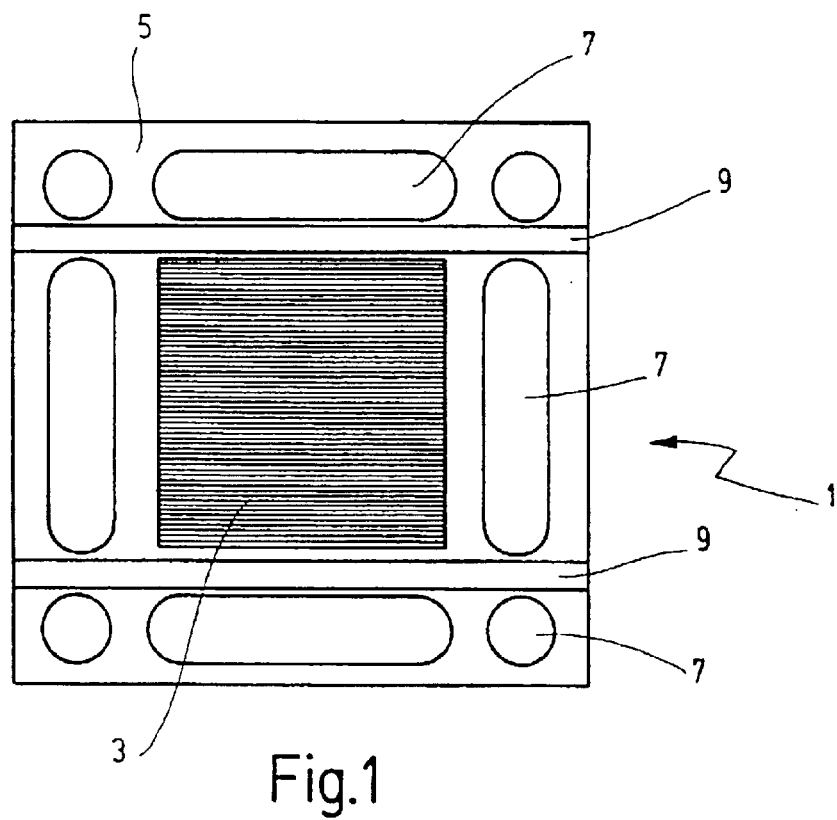
FIG. 1 shows a disk-shaped reactor module.

FIG. 1 shows a reactor module 1, comprising a plurality of hollow fibers arranged in one plane and parallel to each other, which are clamped into a square, disk-shaped frame 5. The frame 5 thus encloses the hollow fibers 3 that are arranged in a single plane on all sides and keeps them spatially fixated. At the same time, the frame two-dimensionally encloses an inside space that contains the ceramic hollow fibers 3, and is divided by said ceramic hollow fibers into one space inside and one space outside of the hollow fibers 3. The frame 5 has integrated openings 7 for the addition and removal of fluids and gases (not shown). Both the space inside the hollow fibers 3 and outside the hollow fibers is in fluid connection with the inlet or outlet openings 7, making it possible to pass fluids, such as gases or preferably liquids, into or out of the capillary inside or outside space in a targeted manner. The frame 5 furthermore includes thermal compensation elements 9 in the form of two recesses that extend parallel to each other over the entire width of the reactor module 1, and in each of which recesses a compensation strip is arranged.

The hollow fibers 3 were produced and surface-modified as follows: N-methyl-morpholine-N-oxide was prepared as a 50% solution in water, into which solution cellulose was added; the cellulose was dispersed, and then part of the water was vacuum-distilled. The resulting suspension is homogenized, and ceramic powder suspended in N-methyl-morpholine-N-oxide is added. Then the residual water is distilled off, and the entire suspension is again homogenized and de-gassed, resulting in a homogeneous spinning mass. In a subsequent spinning process, soaked fibers with a stable, hollow structure are obtained. During the spinning process, the homogeneous spinning mass is transferred into a spinning bath, resulting in a phase inversion of the cellulose that is accompanied by a stabilization of the hollow structure. During the soaking process, water is exchanged for N-methyl-morpholine-N-oxide. The soaked fiber with stabilized hollow structure obtained during the spinning process is dried, which yields a dried base fiber that is sintered, resulting in the hollow fiber 3.

The hollow fibers 3 were coated with a biomatrix—preferably collagen. Then a cell suspension of hepatocytes is applied to the cell carrier frames. By lightly moving the frames, the cells come into contact with the hollow fibers and adhere to the hollow fibers. Then a second layer of collagen can be applied over the cells. The frames, after having been applied with the hepatocytes in this manner, can be cryopreserved in liquid nitrogen for long-term storage.

Figure 2:
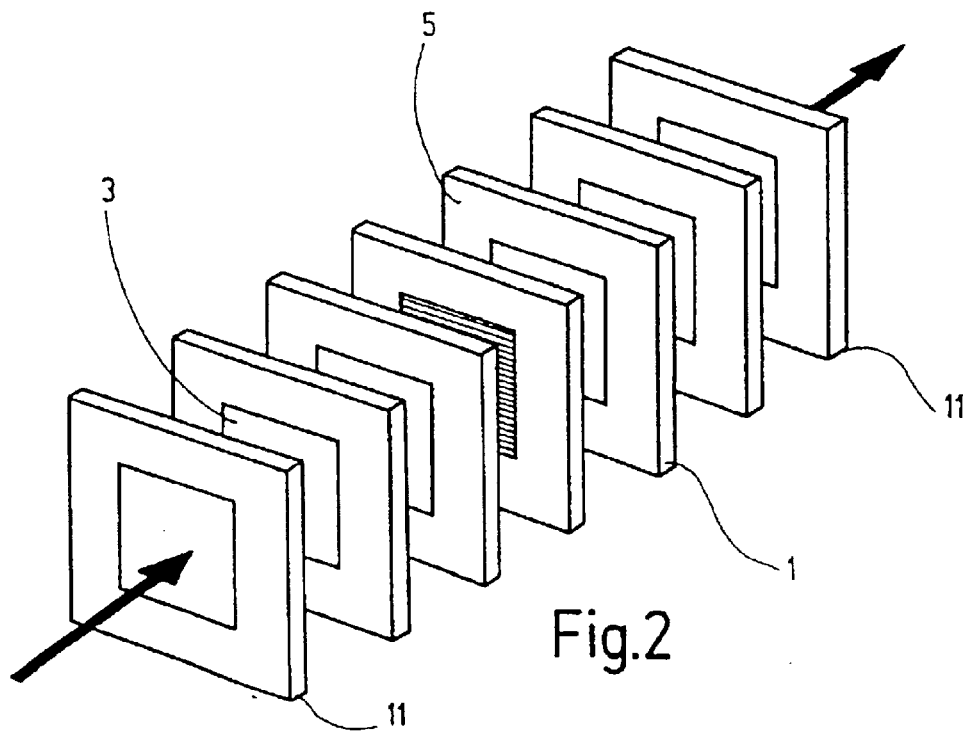
FIG. 2 shows a preferred arrangement of different reactor modules positioned behind each other.

FIG. 2 is a schematic of a potential arrangement of the reactor modules 1. The reactor modules 1 are arranged in parallel planes behind each other, allowing an efficient flow of the body fluid (not shown) of the patient through them in arrow direction. Also shown are sterile filtration modules 11 upstream and downstream from the reactor modules 1 according to the invention, which prevent cells and cell components from being flushed in and out.

Figure 3:
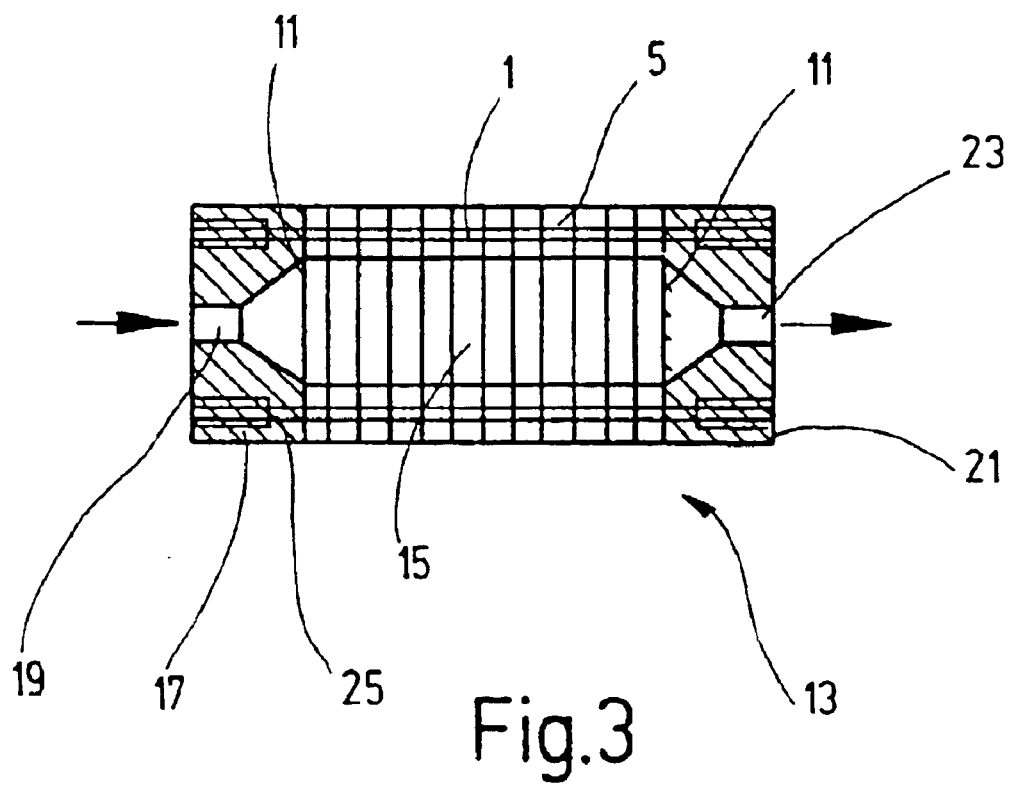
FIG. 3 is a schematic longitudinal section of the construction of a reactor.

FIG. 3 shows a reactor 13 according to the invention. The reactor 13 comprises disk-shaped reactor modules 1 arranged behind each other in parallel planes, whereby the frame 5 of the reactor module 1 at the same time forms the reactor outside wall, the inlet and outlet openings form channels (not shown) in the reactor outside wall, and the ceramic hollow fibers are arranged in the reactor inside space 15. Depending on the construction of the inlet and outlet openings 7 in the used reactor modules 1 and their arrangement in the reactor 13, compartments that are substantially separated in a targeted manner from each other and arranged behind each other can be created, said compartments being characterized by a different cell occupation and/or cultivation conditions. The patient's plasma flows through an inlet opening 19 in a reactor end part, i.e. a terminal area 17, into the reactor 13, passes through a sterile filter 11 and then through the ceramic hollow fibers of the reactor modules 1 in order to then flow out via another sterile filtration module 11 through a reactor end part 21 in the opposite part of the reactor and the outlet opening 23 in this reactor end part.

Figure 4:
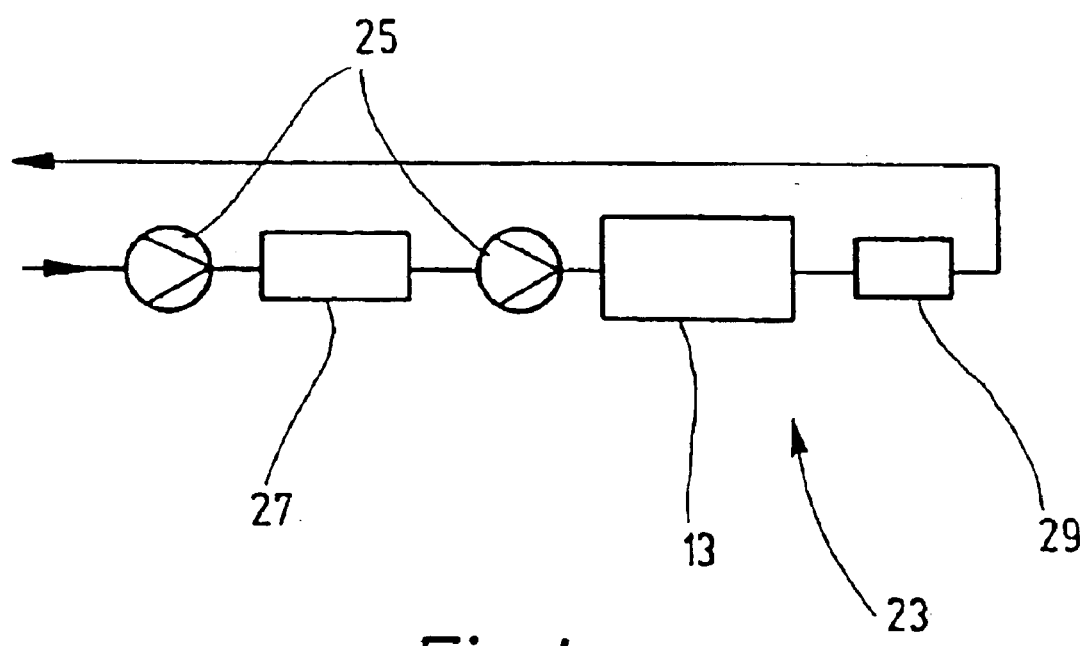
FIG. 4 is a schematic of the construction of an artificial organ.

FIG. 4 shows an artificial liver 23, comprising pumps 25, a plasma separator 27, a reactor 13 according to the invention, and a heat exchanger 29. The blood of a patient (not shown) is brought into circulation via pumps 25 and is passed through a plasma separator 27, in which blood cells are separated. The resulting plasma flows through the reactor 13 according to the invention, in which the hepatocytes that have been immobilized on the ceramic hollow fibers perform their metabolic function. The plasma then flows back into the patient via heat exchanger 29. Like the plasma separator 27, the heat exchanger 29 may also be located inside the reactor 13.

What is claimed as new and desired to be protected by Letters Patent of the United States is:

1. A reactor module, comprising at least one ceramic hollow fiber and at least one biological cell, whereby the at least one ceramic hollow fiber is clamped into a frame of plastic, whereby thermal compensation elements are integrated in the frame of the reactor module, and whereby the at least one biological cell is immobilized on the at least one ceramic hollow fiber.

2. A reactor module according to claim 1, whereby the biological cell is a liver cell.

3. A reactor module according to claim 2, whereby the surface of the hollow fiber is modified.

4. A reactor module according to claim 3, whereby the surface of the hollow fiber is chemically or physically modified.

5. A reactor module according to claim 4, whereby the surface of the hollow fiber is modified by using a low-pressure plasma process.

6. A reactor module according to claim 5, whereby the surface of the hollow fiber includes adhesion promoters.

7. A reactor module according to claim 1, whereby the reactor module is realized in the shape of a disk.

8. A reactor module according to claim 1, whereby the hollow fiber has an inner diameter of 0.1 to 4 mm.

9. A reactor module according to claim 8, whereby the pore size of the hollow fiber is 0.05 to 1 $\mu$m.

10. A reactor module according to claim 9, whereby inlet and/or outlet openings are integrated into the frame of the reactor module.

11. A reactor comprising at least one reactor module according to claim 1 in a housing.

12. A reactor according to claim 11, comprising at least one oxygenator, at least one heat exchanger, and/or at least one sample collection or loading unit.

13. A reactor according to claim 12, whereby the reactor modules are arranged in compartments defined by the arrangement of the inlet and outlet openings.

14. A reactor according to claim 13, whereby different cells are present in the compartments.

15. A reactor according to claim 14, whereby different cultivation conditions exist in the compartments.

* * * * *